United States Patent [19]

Broom et al.

[11] Patent Number: 4,923,856
[45] Date of Patent: May 8, 1990

[54] PENEM COMPOUNDS

[75] Inventors: Nigel J. P. Broom; Gerald Brooks; Steven Coulton, all of Betchworth, England

[73] Assignee: Beecham Group p.l.c., Brentford, United Kingdom

[21] Appl. No.: 286,375

[22] Filed: Dec. 16, 1988

[30] Foreign Application Priority Data

Dec. 18, 1987 [GB] United Kingdom ................ 8729613

[51] Int. Cl.⁵ .................. C07D 499/00; A61K 31/425
[52] U.S. Cl. .................................... 514/192; 514/193; 540/310
[58] Field of Search ................ 540/315, 310; 514/192, 514/193

[56] References Cited

U.S. PATENT DOCUMENTS 4,798,828  1/1989  Osbourne ........................... 514/192
4,826,833  5/1989  Chen et al. ......................... 540/310

FOREIGN PATENT DOCUMENTS 0154132  9/1985  European Pat. Off. .

*Primary Examiner*—Nicholas S. Rizzo
*Attorney, Agent, or Firm*—Hopgood, Calimafde, Kalil, Blaustein & Judlowe

[57] ABSTRACT

Compounds of the general formula (II):

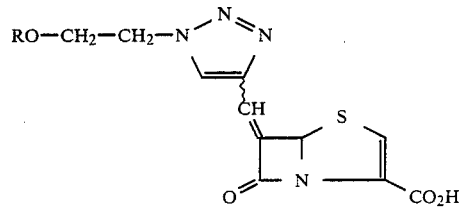

and pharmaceutically acceptable salts and in-vivo hydrolysable esters thereof, in which
  R denotes a hydrogen atom or an in vivo hydrolysable acyl group;
  and the wavy line denotes either the E- or Z-isometric position,
are novel compounds which exhibit $\beta$-lactamase inhibitory action and have antibacterial properties.

11 Claims, No Drawings

PENEM COMPOUNDS

This invention relates to novel β-lactam compounds and in particular to novel 6-(substituted methylene) penems which have β-lactamase inhibitory and antibacterial properties. The compounds are therefore useful in the treatment of antibacterial infections in humans or animals, either alone or in combination with other antibiotics.

European Patent Publication EP No. 0 154 132 A (Beecham; published 11 Sept. 1985) (the contents of which is incorporated herein by reference thereto) describes compounds of the general formula I, which exhibit β-lactamase inhibitory action and synergistic activity:

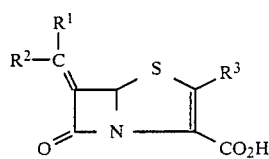

and their pharmaceutically acceptable salts and in-vivo hydrolysable esters, in which
one of $R^1$ and $R^2$ denotes hydrogen,
the other of $R^1$ and $R^2$ denotes an unsubstituted or substituted five-membered hetero-aromatic ring bonded through a carbon atom thereof and having one hetero-atom selected from nitrogen, oxygen and sulphur and additionally having from one to three nitrogen atoms, and
$R^3$ denotes hydrogen or an organic group.

Such compounds are advantageously in the form of the 5R-isomer, that is to say in the form of structure IA:

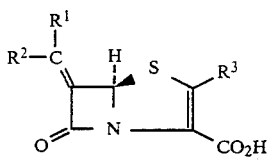

Among the compounds described in EP No. 0 154 132 A are compounds of the general formula I in which $R^1$ or $R^2$, preferably $R^1$, denotes a triazolyl group, especially a 1-substituted-1,2,3-triazol-4-yl group, and the other of $R^1$ and $R^2$ denotes hydrogen. More specifically, the said publication describes the compound of the general formula IA in which $R^1$ denotes a 1-methyl-1,2,3-triazol-4-yl group and each of $R^2$ and $R^3$ denotes hydrogen, namely:

(5R) (Z)-6-(1-methyl-1,2,3-triazol-4-yl-methylene) penem-3-carboxylic acid;

as well as its pharmaceutically acceptable salts and in-vivo hydrolysable esters.

Further crystalline and hydrated forms of that compound and its salts are described in European Patent Publication EP No. 0 210 814 A (Beecham; published 04 Feb. 1987) (the contents of which is incorporated herein by reference thereto).

Further details of suitable esters and salts of compounds of the general formula I, and also details of methods of preparing the compounds and the manner of formulating them into pharmaceutical compositions and using them for therapeutic treatment, are given EP No. 0 154 132 A.

Improved methods of preparing the compounds of the general formula I are described in European Patent Publication EP No. 0 232 966 A (Beecham; published 19 Aug. 1987) (the contents of which is incorporated herein by reference thereto).

It has now been found that 6-[1-(2-hydroxyethyl)-1,2,3-triazol-4-yl-methylene]penem exhibits improved activity as compared with the previously described compounds, and that compound may also usefully be provided in the form of pro-drugs.

Accordingly, the present invention provides a compound of the general formula II

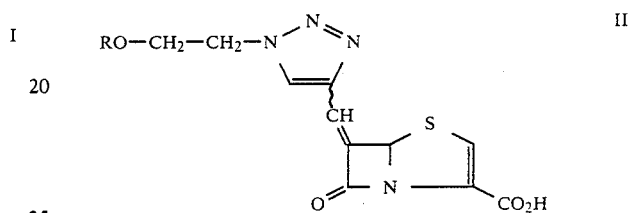

or a pharmaceutically acceptable salt or in vivo hydrolysable ester thereof in which
R denotes a hydrogen atom or an in vivo hydrolysable acyl group;
and the wavy line denotes either the E- or Z-isomeric position.

The acyl group R is in vivo hydrolysable such that on administration of the compound to a patient, the ester group RO— hydrolyses in the human body to produce the parent hydroxyethyltriazolyl compound. Thus, the compounds in which R denotes an acyl group are pro-drugs of the compound in which R denotes hydrogen, and its salts and esters.

The in vivo hydrolysable acyl group denoted by R may suitably be a formyl group, an alkanoyl group, especially a $(C_{1-6})$alkanoyl group, which may optionally be substituted, or an arylcarbonyl group, especially a benzoyl group, which may optionally be substituted.

Examples of suitable optional substituents for the above-mentioned alkanoyl and arylcarbonyl groups include $(C_{1-6})$alkyl, $(C_{2-6})$alkenyl, $(C_{2-6})$alkynyl, $(C_{3-7})$cycloalkyl, $(C_{3-7})$cycloalkyl$(C_{1-6})$alkyl, aryl, aryl$(C_{1-6})$alkyl, $(C_{1-6})$alkanoyl, $(C_{1-6})$alkanoyloxy, heterocyclyl, amino, $(C_{1-6})$alkanoylamino, (mono or di)-$(C_{1-6})$alkylamino, hydroxy, $(C_{1-6})$alkylsulphinyl, $(C_{1-6})$alkylsulphonyl, heterocyclylthio, arylthio, sulphamoyl, carbamoyl, amidino, guanidino, nitro, halogen, carboxy, carboxy salts, carboxy esters, arylcarbonyl and heterocyclylcarbonyl groups.

When any such substituent is or includes a carboxy salt or carboxy ester moiety, that substituent is suitably a pharmaceutically acceptable salt or pharmaceutically acceptable ester.

The term 'heterocyclyl' as used herein includes aromatic and non-aromatic, single and fused, rings containing up to four hetero-atoms in each ring selected from oxygen, nitrogen and sulphur, which rings may be unsubstituted or substituted by up to three groups selected from halogen, $(C_{1-6})$alkyl, $(C_{1-6})$alkoxy, halo$(C_{1-6})$alkyl, hydroxy, amino, carboxy, $(C_{1-6})$alkoxycarbonyl $(C_{1-6})$alkoxycarbonyl$(C_{1-6})$alkyl, aryl, $(C_{1-6})$alkylthio, arylthio, mercapto and oxo groups.

The term 'aryl' as used herein includes phenyl and naphthyl, which may be unsubstituted or substituted by up to five, preferably up to three, groups selected from halogen, $(C_{1-6})$alkyl, phenyl, $(C_{1-6})$alkoxy, halo$(C_{1-6})$alkyl, hydroxy, amino, nitro, carboxy, $(C_{1-6})$alkoxycarbonyl,$(C_{1-6})$alkoxycarbonyl$(C_{1-6})$alkyl, $(C_{1-6})$alkylcarbonyloxy $(C_{1-6})$alkylcarbonyl $(C_{1-6})$alkylthio, arylthio, and mercapto groups.

Suitable pharmaceutically acceptable salts and in-vivo hydrolysable esters of the compounds of the general formula II are those salts and ester moieties described in the above-mentioned EP No. 0 154 132 A.

Examples of suitable in vivo hydrolysable ester groups include acetoxymethyl, pivaloyloxymethyl, α-acetoxyethyl, α-acetoxybenzyl, α-pivaloyloxyethyl, ethoxycarbonyloxymethyl, α-ethoxycarbonyloxyethyl, dimethylaminomethyl, diethylaminomethyl, phthalidyl and dimethoxyphthalidyl groups.

Examples of suitable pharmaceutically acceptable salts of the 3-carboxylic acid group of the compound of formula II include metal salts, e.g. aluminium salts, alkali metal salts (e.g. sodium or potassium salts), alkaline earth metal salts (e.g. calcium or magnesium salts), ammonium salts, and substituted ammonium salts, for example those with lower alkylamines (e.g. triethylamine), hydroxy-lower alkylamines (e.g. 2-hydroxyethylamine), di(2-hydroxyethyl)amine or tri(2-hydroxyethyl)amine), cycloalkylamines (e.g. dicyclohexylamine), or with procaine, and also dibenzylamine, N,N-dibenzylethylenediamine, 1-ephenamine, N-ethylpiperidine, N-benzyl-β-phenethylamine, dehydroabietylamine, N,N'-bishydro abietylethylene-diamine, bases of the pyridine type (e.g. pyridine, collidine and quinoline), and other amines which have been or can be used to form salts with penicillins.

The compounds of the general formula II and also the salts and esters thereof may exist in two optically active forms and it is to be understood that both such forms as well as racemic mixtures thereof are embraced by the present invention. It is believed that the more active form is that of structure IIA:

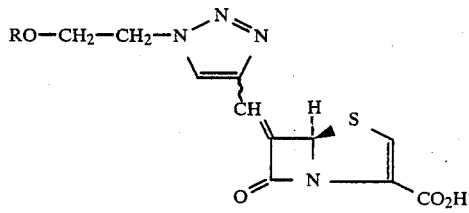

IIA in which R is defined as above.

Moreover, the compounds of the general formula II and also the salts and esters thereof may exist in two isomeric forms at the methylene group, that is to say at the 8-position, namely the E- and Z-isomeric forms. The Z-isomer is preferred as generally being the more active form.

Compounds according to the invention include:
(5R)-(Z)-6-[1-(2-acetoxyethyl)-1,2,3-triazol-4-ylmethylene]penem-3-carboxylic acid;
(5R)-(Z)-6-[1-(2-trimethylacetoxyethyl)1-2,3-triazol-4-ylmethylene]penem-3-carboxylic acid;
(5R)-(Z)-6-(1-[2-(3-carboxylpropanoyloxy)-ethyl]-1,2,3-triazol-4-ylmethylene)penem-3-carboxylic acid; and
(5R)-(Z)-6-[1-(2-hydroxyethyl)-1,2,3-triazol-4-ylmethylene]penem-3-carboxylic acid;

or a pharmaceutically acceptable salt or in vivo hydrolysable ester thereof.

Examples of individual compounds according to the invention include:
sodium (5R)-(Z)-6-[1-(2-hydroxyethyl)-1,2,3-triazol-4-ylmethylene]penem-3-carboxylate;
sodium (5R)-(Z)-6-[1-(2-hydroxyethyl)-1,2,3-triazol-4-ylmethylene]penem-3-carboxylate monohydrate;
sodium (5R)-(Z)-6-[1-(2-acetoxyethyl)-1,2,3-triazol-4-ylmethylene]penem-3-carboxylate;
sodium (5R)-(Z)-6-[1-(2-trimethylacetoxyethyl)-1-2,3-triazol-4-ylmethylene]penem-3-carboxylate; and
disodium (5R)-(Z)-6-(1-[2-(3-carboxylatopropanoyloxy)-ethyl]-1,2,3-triazol-4-ylmethylene)penem-3-carboxylate.

The compounds according to the invention are advantageously provided in crystalline form, which will in some cases also be in hydrated form.

A compound of the general formula II given above, and more particularly such a compound in which R denotes a hydrogen atom, may be prepared using the methods described in the above-mentioned EP No. 0 232 966 A. In particular, such compounds may be prepared using the procedure described as 'Route F' in that publication in which $R^{12}$ denotes the moiety

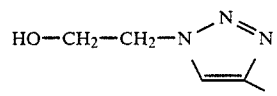

III in which the hydroxy group may optionally be protected.

Thus, a 6-halopenem may be reacted with an aldehyde of the formula

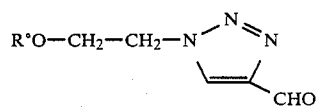

IV in which
$R^o$ denotes a hydroxy-protecting group, and,
if $R^o$ does not correspond to the desired group R, subsequently subjecting the product to reductive elimination and removal of the hydroxy-protecting group to give compounds of the general formula (II) in which R denotes a hydrogen atom, and thereafter if desired esterifying in a conventional manner to give a compound of the general formula (II) in which R denotes an acyl group.

Examples of suitable hydroxy protecting groups $R^o$ include trityl (triphenylmethyl), dimethoxytrityl (4,4'-dimethoxytriphenylmethyl), trimethoxytrityl (4,4',4''-trimethoxytriphenylmethyl), trimethylsilyl, t-butyldimethylsilyl, t-butyldiphenylsilyl, benzyloxycarbonyl, p-methoxybenzyloxycarbonyl, 2-(trimethylsilyl)ethoxycarbonyl, acetonyloxycarbonyl, and allyloxycarbonyl groups.

Moreover, in certain cases, the desired in-vivo hydrolysable acyl group R may be used as the hydroxy-protecting group $R^o$, for example a formyl group or an acetyl group.

An aldehyde of the general formula IV may, for example, conveniently be prepared from an alkyl 1-(2-hydroxyethyl)-1,2,3-triazole-4-carboxylate (prepared according to the method of S. M. Spojanovic, Collect.

Czeck. Chem. Comm., 1967, 32, 2155), by reduction of the carboxylate group to a primary alcohol group, and then oxidation to the desired aldehyde function, with the hydroxy-protecting group $R^o$ being introduced in a conventional manner, for example by reaction with di- or tri-methoxytrityl chloride, either initially or after formation of the aldehyde function.

Following reaction of the aldehyde of the formula IV with the 6-halopenem, and subsequent reductive elimination of the halohydrin thus formed, to give a 6-methylene-penem, as described in EP No. 0 232 966 A, the hydroxy protecting group may (unless it equates to the desired in-vivo hydrolysable acyl group R) be removed in a conventional manner, for example by acidic hydrolysis or, in the case of silyl protecting groups, by treatment with tetra-n-butylammonium fluoride/acetic acid in tetrahydrofuran, to give the desired compound of the formula II in which R denotes hydrogen.

The hydroxy compound thus obtained may then be esterified in a conventional manner to give compounds of the general formula II in which R denotes an acyl group.

Alternatively, the desired acyl group R could be introduced into the aldehyde (replacing any initial protecting group $R^o$) prior to its reaction with the 6-halopenem.

As indicated previously, the hydroxyethyl compound according to the invention (R=H) has β-lactamase inhibitory activity, and it and its pro-drugs are useful in the treatment of bacterial infections.

Accordingly the present invention also provides a method of treating bacterial infections which comprises administering to a human or animal in need of an antibacterially effective amount or a β-lactamase inhibitory amount of a compound of general formula II.

Advantageously, said compound is administered to said human or animal in conjunction with the prior, simultaneous or subsequent administration of a penicillin, cephalosporin or other β-lactamase antibiotic.

Accordingly, according to a further aspect, the present invention provides a pharmaceutical composition comprising a compound according to the invention in admixture or conjunction with a pharmaceutically acceptable carrier. The composition may also comprise a penicillin, cephalosporin or other β-lactam antibiotic.

Details of formulating such compositions and using the compound according to the invention are given in EP No. 0 154 132 A.

The following examples illustrate the present invention. All temperatures quoted in the examples are in °C.

The following Scheme 1 outlines the reaction sequence through Preparations 1 to 4 and Example 1(a)-(c). In the formulae in Scheme 1:
DMT denotes 4,4'-dimethoxytrityl, and
pMB denotes p-methoxybenzyl.

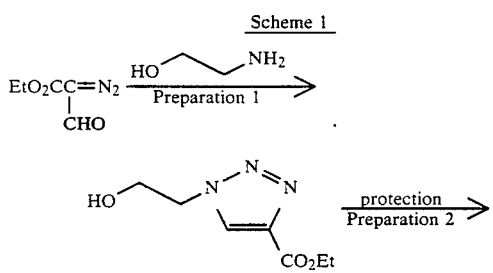

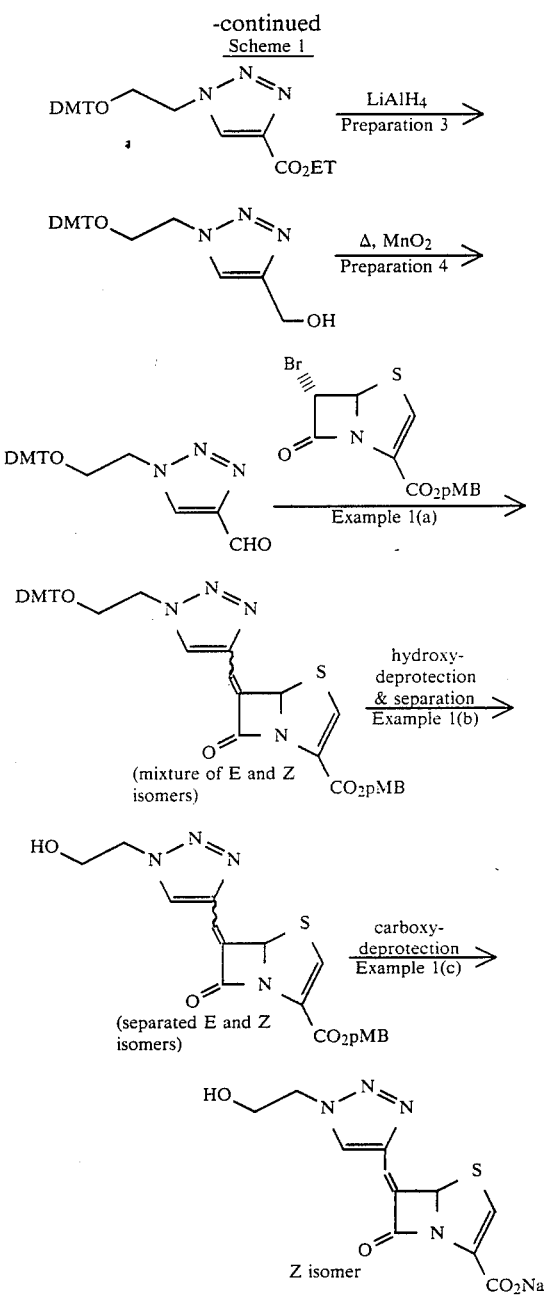

PREPARATION 1

Ethyl 1-(2-Hydroxyethyl)-1,2,3-triazole-4-carboxylate

A solution of ethanolamine (60 ml, 1 mole) in methanol (320 ml) at 5° was treated with formic acid until a pH of 5 was obtained. A solution of ethyl α-formyldiazoacetate (crude, approximately 0.3 mole) in methanol (320 ml) was then added and the mixture stirred at room temperature for two days. The mixture was then evaporated, chloroform (1 liter), then water (200 ml) was added and the mixture was treated with sodium bicarbonate until a pH of 7 was reached. The phases were separated and the aqueous phase saturated with sodium chloride and extracted with chloroform (6×300 ml). The combined organic phases were dried (MgSO₄), filtered and evaporated. The residue was then dissolved in toluene (approximately 100 ml). The resulting crystalline solid was filtered, washed with ether and dried to provide the title compound (41.6 g) as a solid; $\nu_{max}$ (nujol) 3320, 3140, 1725 cm$^{-1}$; δ (CDCl$_3$), 1.38 (3H, t, J 7.5 Hz), 4.00–4.80 (7H, m, becomes 6H, m on D$_2$O exch), 8.40 (1H, s). This material was pure enough for further synthetic progression.

PREPARATION 2

Ethyl 1-2-(4,4'-Dimethoxytrityloxy)ethyl]-1,2,3-triazole-4-carboxylate

A solution of the product from Preparation 1 (20.3 g) in dry dichloromethane (200 ml) at 5° was sequentially treated with triethylamine (15.4 ml) and 4,4'-dimethoxytrityl chloride (37.4 g). The reaction mixture was warmed to room temperature and, after 1 hour, ethyl acetate (800 ml) was added. The mixture was washed with 0.2N HCl, brine, then dried (MgSO$_4$) and evaporated. The residue was chromatographed on silica eluting with ethyl acetate/hexane mixtures to provide the title compound as an amorphous solid (41.2 g); $\nu_{max}$ (CHCl$_3$) 1725 cm$^{-1}$; δ (CDCl$_3$), 1.40 (3H, t, J 6.5 Hz), 3.44–3.80 (m) overlaying 3.68 (s) (together 8H), 4.35–4.69 (4H, m), 6.82 (4H, d, J 9.0 Hz), 7.25 (4H, d, J 9.0 Hz), 7.30 (5H, s), 8.22 (1H, s).

PREPARATION 3

1-[2-(4,4'-Dimethoxytrityloxy)ethyl]-4-hydroxymethyl-1,2,3-triazole

A solution of the product from Preparation 2 (40 g) in tetrahydrofuran (400 ml) at 5° under argon was treated with lithium aluminium hydride (4.67 g). After 30 minutes the cooling bath was removed and after a further hour water (175 ml) was carefully added. The resulting gel was treated with ethyl acetate (2 liters) and filtered. The filtrate was washed with water and brine, then dried and evaporated. The residue was chromatographed on silica eluting with ethyl acetate/hexane mixtures to give the title compound (34.5 g) as an amorphous solid; δ (CDCl$_3$) 2.93 (1H, bs), 3.30–3.55 (2H, m), 3.77 (6H, s), 4.30–4.60 (2H, m), 4.81 (2H, s), 6.83 (4H, d, J 9.0 Hz), 7.23 (4H, d, J 9.0 Hz), 7.27 (5H, bs), 7.67 (1H, s).

PREPARATION 4

1-[2-(4,4'-Dimethoxytrityloxy)ethyl]-1,2,3-triazole-4-carboxaldehyde

A solution of the product from Preparation 3 (34.5 g) in benzene (600 ml) was treated with manganese dioxide (48.3 g) and the mixture was refluxed with provision for the azeotropic removal of water (Dean and Stark apparatus containing 4A molecular sieves) for 18 hours. The reaction mixture was diluted with dichloromethane (1.5 liters) and filtered through Kieselguhr, washing the pad well with dichloromethane. The filtrate was evaporated and chromatographed on silica eluting with ethyl acetate/hexane mixtures to give the title compound (27 g) as an amorphous solid. $\nu_{max}$ (CHCl$_3$) 1705 cm$^{-1}$; δ (CDCl$_3$), 3.60 (2H, t, J 4.5 Hz), 3.76 (6H, s), 4.50 (2H, t, J 4.5 Hz), 6.81 (4H, d, J 8.5 Hz), 7.22 (4H, d, J 8.5 Hz), 7.29 (5H, s), 8 21 (1H, s), 10.15 (1H, s).

EXAMPLE 1(a)

(5R) p-Methoxybenzyl 6-(1-[2-(4,4'-Dimethoxytrityloxy)ethyl-1,2,3-triazole-4-ylmethylene)penem-3-carboxylate A solution of diphenylamine (6.03 g) in dry tetrahydrofuran (THF) (150 ml) at −10° under argon was treated with a solution of n-butyl lithium (1.5 M, 21.8 ml) in hexane. After 10 minutes the reaction mixture was cooled to −78° and sequentially treated with a solution of (5R,6S) p-methoxybenzyl 6-bromopenem-3-carboxylate (11.35 g) (EP No. 0 232 966 A) in THF (50 ml), then a solution of the product from Preparation 4 (13.5 g) in THF (50 ml) and finally acetic anhydride (9.61 ml). The cooling bath was removed and the reaction mixture was allowed to reach room temperature. The reaction mixture was then diluted with ethyl acetate (1 liter), washed with saturated sodium bicarbonate solution, and brine, then dried (MgSO$_4$) and evaporated.

The residue was dissolved in dimethylformamide (200 ml) and treated with ammonium chloride (4.6 g), N,N,N',N'-tetramethylethylenediamine dihydrochloride (4.09 g) and zinc powder (5.32 g), and then vigorously stirred for 1 hour. The reaction mixture was then diluted with ethyl acetate (1.5 liter) washed with 0.2N HCl (1 liter), water (1 liter), saturated sodium bicarbonate solution (500 ml) and brine (500 ml), then dried (MgSO$_4$) and evaporated. The residue was chromatographed on silica eluting with ethyl acetate/hexane mixtures to give a 1:5 mixture of E and Z isomers of the title compound as a yellow amorphous solid (13.75 g); $\nu_{max}$ (CHCl$_3$) 1780, 1710, 1615 cm$^{-1}$; δ (CDCl$_3$) inter alia 6.43 (≃H, s, C5-H; E isomer), 6.63 (4/5H, d, J 0.8 Hz, C5-H; Z isomer), 7.81 (4/5H, s, C5'-H; Z isomer), 8.92 (≃H, s, C5'-H; E isomer).

EXAMPLE 1(b)

(5R) p-Methoxybenzyl 6-[1-(2-Hydroxyethyl)-1,2,3-triazol-4-ylmethylene)-penem-3-carboxylate A solution of the mixture of products from Example 1(a) (13.75 g) in dichloromethane (1 liter) at 5° C. under argon was treated with formic acid (27.5 ml). After 1 hour water (300 ml) was added, followed by a solution of sodium hydroxide (27.5 g) in water (50 ml). The pH of the aqueous layer was adjusted to pH 9 by the addition of more sodium hydroxide solution. The organic phase was separated, washed with water (200 ml), brine (200 ml), then dried (MgSO$_4$) and evaporated. On standing the residue was observed to crystallise; ethyl acetate (100 ml) was added and the mixture warmed. The resulting cyrstalline solid (1.89 g) was collected by filtration and dried. This material was identified as the Z-isomer of the title compound; mp 137°–140° (yellow needles from ethyl acetate); [α]$_D^{20}$+420° (c 0.5 in DMSO); $\lambda_{max}$ (2%) CHCl$_3$/EtOH, 288 nm (εm 25,100); $\nu_{max}$ (nujol) 3500, 1780, 1695 cm$^{-1}$; δ (d$_6$-DMSO), 3.70–3.85 (m) overlaying 3.76 (s) (together 5H), 4.47 (2H, t, J 5.2 Hz), 5.09 (1H, t, J 5.2 Hz), 5.16 (2H, s), 6.67 (1H, d, J 0.8 Hz), 6.94 (2H, d, J 8.6 Hz), 7.35 (s) overlaying 7.37 (d, J 8.3 Hz) (together 3H), 7.73 (1H, s), 8.42 (1H, s). (Found C, 55.1; H, 4.3; N, 13.7; S, 7.7. C$_{19}$H$_{18}$N$_4$O$_5$S requires C, 55.1; H, 4.4; N, 13.5; S, 7.7%).

The mother liquors were concentrated and chromatographed on silica eluting with ethyl acetate/hexane mixtures to give a mixture of E- and Z-isomers of the title compound. A further quantity (0.86 g) of the Z-isomer was obtained by careful crystallisation of this mixture from ethyl acetate/hexane. Continued elution of the column gave the Z-isomer of the title compound (1.19 g).

A pure sample of the E-isomer of the title compound was obtained by careful chromatography of the mixed fractions on silica eluting with ethyl acetate/chloroform mixtures; mp 160°–2° (yellow plates from ethyl acetate); $[\alpha]_D^{24} -283°$ (c 0.5 in DMSO); $\lambda_{max}$ (2% CHCl$_3$/ETOH) 297 nm ($\epsilon_m$ 19,300), 350 (2, 100); $\nu_{max}$ (nujol) 3300, 1760, 1710 cm$^{-1}$; δ (d$_6$-DMSO), 3.70–3.83 (m) overlaying 3.76 (s) (together 5H), 4.50 (2H, t, J 5.2 Hz), 5.08 (1H, t, J 5.2 Hz), 5.15 (2H, s), 6.53 (1H, s), 6.95 (2H, d, J 8.7 Hz), 7.23 (1H, s), 7.36 (2H, d, J 8.6 Hz), 7.82 (1H, s), 8.74 (1H, s). (Found C, 55.1; H, 4.6; N, 13.3; S, 7.9. C$_{19}$H$_{18}$N$_4$O$_5$S requires C, 55.1; H, 4.6; N, 13.5; S, 7.7%).

EXAMPLE 1(c)

Sodium
(5R)-(Z)-6-1-(2-hydroxyethyl)-1,2,3-triazol-4-ylmethylene]penem-3-carboxylate p-Methoxybenzyl (5R)-(Z)-6-[1-(2-hydroxyethyl)-1,2,3-triazol-4-ylmethylene]penem-3-carboxylate (3.0 g) was dissolved in dichloromethane (225 ml) and added over a period of 10 minutes, to a stirred solution of aluminium trichloride (2.43 g) in dichloromethane (18 ml) and anisole (72 ml), at −40° C., under an atmosphere of argon. After the addition was complete, the resulting solution was stirred at −40° C. for a further 10 minutes. Disodium hydrogen phosphate solution (0.5 M; 246 ml) was then added, the cooling bath removed and the resulting suspension stirred vigorously at ambient temperature for 15 min. The suspension was filtered through Celite, and washed well with water. The aqueous layer was washed with ether, separated, and carefully adjusted to pH 2.0, by the addition, with stirring, of 2N sulphuric acid. The resulting solution was cooled in an ice-bath for 15 min., before filtering through coarse grade glass fibre filter paper. The solid was washed with ice-cold water, before being suspended in water (200 ml). The resulting suspension was carefully adjusted to pH 7.0 by the careful addition of 0.1N sodium hydroxide solution. The solution was filtered through glass fibre filter paper and lyophilised to yield the title compound as a yellow fluffy solid (1.46 g), $\lambda_{max}$(H$_2$O) 281 nm ($\epsilon$23,935); $[\alpha]_D^{20} +423°$ (c 1.0, H$_2$O).

EXAMPLE 1(d)

Sodium
(5R)-(Z)-6-1-(2-hydroxyethyl)-1,2,3-triazol-4-ylmethylene]penem-3-carboxylate monohydrate A sample of the product of Example 1(c) (400 mg) was dissolved in water and purified by column chromatography over HP20SS, eluting with water. The column fractions were monitored by u.v. spectroscopy, and those fractions containing the desired product were combined and the solution evaporated to small volume. The product was then precipitated by the addition of excess isopropanol. The resulting yellow solid was collected by filtration, washed with acetone and dried in vacuo. The title compound was thus obtained, as a yellow crystalline solid (270 mg), $\lambda_{max}$ (H$_2$O) 366 ($\epsilon$1879), 283 nm ($\epsilon$21,260); $\nu_{max}$ (KBr) 3386 (broad), 1756, 1688, 1599 cm$^{-1}$; $[\alpha]_D^{20} +439°$ (c 1.0, H$_2$O); $\delta_H$ (D$_2$O) 3.98 (2H, t, J 5.0 Hz), 4.56 (2H, t, J 5.0 Hz), 6.61 (1H, d, J 0.6 Hz), 7.04 (1H, s), 7.21 (1H, s), 8.24 (1H, s), (Found: C, 39.7; H, 3.1; N, 16.35; S, 9.65; Na, 6.95. C$_{11}$H$_9$N$_4$O$_4$SNa.H$_2$0 requires: C, 39.5; H, 3.3; N, 16.75; S, 9.6; Na, 6.9%).

EXAMPLE 2

Sodium
(5R)-(Z)-6-[1-(2-acetoxyethyl)-1,2,3-triazol-4-ylmethylene]penem-3-carboxylate Acetic anhydride (0.12 ml, 1.2 mmol) was added to a solution containing α-methoxybenzyl (5R)-(Z)-6-[1-(2-hydroxyethyl)-1,2,3-triazol-4-ylmethylene]penem-3-carboxylate (0.21 g, 0.5 mmol) (Example 1(b)), triethylamine (0.16 ml, 1.2 mmol), 4-dimethylaminopyridine (catalytic amount) and dichloromethane (50 ml). After 15 min at 20° C., the resulting solution was washed with 5% aqueous citric acid, saturated aqueous sodium chloride, saturated aqueous sodium bicarbonate and again with saturated aqueous sodium chloride, dried (MgSO$_4$), and evaporated under reduced pressure to give a yellow oil which was purified by chromatography on silicagel eluting with ethyl acetate/hexane mixtures to give p-methoxybenzyl (5R)-(Z)-6-[1-(2-acetoxyethyl)-1,2,3-triazol-4-methylene]penem-3-carboxylate as a yellow oil; 0.22 g (96%); δ ppm (CDCl$_3$) 2.0 (3H, s), 3.8 (3H, s), 4.6 (4H, m), 5.2 (2H, s), 6.6 (1H, s), 6.9 (2H, d, J 9 Hz), 7.1 (1H, s), 7.3 (1H, s), 7.4 (2H, d, 9 Hz), 7.9 (1H, s).

A solution of this compound (0.22 g, 0.5 mmol) in dichloromethane (4 ml) was added to a solution containing aluminium (III) chloride (0.2 g, 1.6 mmol), dichloromethane (2 ml), and anisole (4 ml) at −40° C. After 20 min at −40° C., aqueous disodium hydrogen phosphate (0.5 M, 40 ml, 20 mmol) was added. The resulting mixture was filtered and separated and the aqueous part washed twice with ether, then evaporated under reduced pressure and the resulting residue purified by chromatography on HP20-SS, eluting with aqueous acetone mixtures. Appropriate column fractions were evaporated under reduced pressure, the resulting residues dissolved in water, adjusted to pH 7 and freeze-dried, to give the title compound as a yellow powder; 0.10–0.11 g (55–61%); $[\alpha]D^{20} = +380°$ (c, 0.1, H$_2$O); $\nu_{max}$ (KBr) 1740, 1600 cm$^{-1}$; $\lambda_{max}$ (H$_2$O) 281 ($\epsilon_m$22,600) and 364 ($\epsilon_m$1,800) nm; δppm (D$_2$O) 2.0 (3H, s), 4.5 (2H, t, J 5 Hz), 4.8 (2H, t, J 5 Hz), 6.6 (1H, s), 7.0 (1H, s), 7.2 (1H, s), 8.3 (1H, s).

EXAMPLE 3

Sodium
(5R)-(Z)-6-1-(2-trimethylacetoxyethyl)-1-2,3-triazol-4-ylmethylene1penem-3-carboxylate Using a procedure analogous to that of Example 2, trimethylacetyl chloride (0.14 ml, 1.2 mmol) was used to prepare p-methoxybenzyl (5R)-(Z)-[1-(2-trimethylacetoxyethyl)-1,2,3-triazol-4-ylmethylene]penem-3-carboxylate as a yellow oil; 0.16–0.17 g (67–71%); ppm (CDCl$_3$) 1.2 (9H, s), 3.8 (3H, s), 4.5 (4H, m), 5.2 (2H, s), 6.6 (1H, s), 6.9 (2H, d, J 9 Hz), 7.1 (1H, s), 7.3 (1H, s), 7.4 (2H, d, J 9 Hz), 7.8 (1H, s).

This was converted, analogously to Example 2, to the title compound, obtained as a yellow powder; 0.18 g of ester gave 0.04–0.08 g (28–53%); $[\alpha]D^{20} = +254°$ (c, 1, H$_2$O); $\nu_{max}$ (KBr) 1760, 1730, 1600 cm$^{-1}$; $\lambda_{max}$ (H$_2$O) 282 ($\epsilon_m$20,000) and 368 ($\epsilon_m$ 2,000) nm; δppm (D$_2$O) 1.1 (9H, s), 4.5 (2H, t, J 5 Hz), 6.6 (1H, s), 7.0 (1H, s), 7.2 (1H, s), 8.3 (1H, s).

EXAMPLE 4

Disodium (5R)-(Z)-6-(1-[2-(3-carboxylatopropanoyloxy)ethyl]-1,2,3-triazol-4-ylmethylene]penem-3-carboxylate Using a procedure analogous to that of Example 2, 2-(p-methoxybenzyloxycarbonyl)propanoyl chloride (0.29 g, 1.2mmol) was used to prepare p-methoxybenzyl (5R)-(Z)-6-(1-[2-(3-p-methoxybenzyloxycarbonyl-propanoyloxy)ethyl]-1,2,3-triazol-4-ylmethylene)-penem-3-carboxylate as a yellow oil; 0.36 g (95%); $\delta$ppm (CDCl$_3$) 2.6 (4H, s), 3.8 (6H, s), 4.5 (4H, bs), 5.1 (2H, s), 5.2 (2H, s), 6.6 (1H, s), 6.9 (2H, d, J 9 Hz), 7.0 (1H, s), 7.1 (1H, s), 7.3 (1H, s), 7.4 (2H, d, J 9 Hz), 8.0 (1H, s).

This was converted, analogously to Example 2, to the title compound, obtained as orange rhombs; 0.64 g of ester gave 0.034 g (8%); $[\alpha]D^{20} = +235°$ (c, 0.2, H$_2$O); $\nu_{max}$ (KBr) 1770, 1580 cm$^{-1}$; $\delta$ppm (D$_2$O) 2.4 (2H, t, J 6 Hz), 2.6 (2H, t, J 6 Hz), 4.5 (2H, t, J 5 Hz), 6.7 (1H, s), 7.0 (1H, s), 7.2 (1H, s), 8.3 (1H, s).

We claim:

1. A compound of formula II:

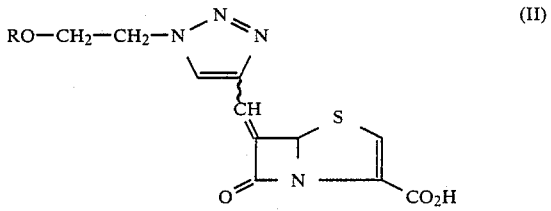

or a pharmaceutically acceptable salt or in vivo hydrolysable ester thereof in which
R denotes a hydrogen atom or an in vivo hydrolysable acyl group;
and the wavy line denotes either the E- or Z-isomeric position.

2. A compound according to claim 1, wherein R is a formyl group, an optionally substituted alkanoyl group or an optionally substituted arylcarbonyl group, wherein:
the substituents for the alkanoyl or arylcarbonyl group are selected from one or more of the following groups: (C$_{1-6}$)alkyl, (C$_{2-6}$)alkenyl, (C$_{2-6}$)alkynyl, (C$_{3-7}$)cycloalkyl, (C$_{3-7}$)cycloalkyl (C$_{1-6}$)alkyl, aryl, aryl(C$_{1-6}$)alkyl, (C$_{1-6}$)alkanoyl, (C$_{1-6}$)alkanoyloxy, heterocyclyl, amino, (C$_{1-6}$)alkanoylamino, (mono or di)- (C$_{1-6}$)alkylamino, hydroxy, (C$_{1-6}$)alkylsulphinyl, (C$_{1-6}$)alkylsulphonyl, heterocyclothio, arylthio, sulphamoyl, carbamoyl, amidino, guanidino, nitro, halogen, carboxy, carboxy salts, carboxy esters, arylcarbonyl, and heterocyclylcarbonyl;
aryl is defined as phenyl or naphthyl, unsubstituted or substituted by up to five groups selected from halogen, phenyl, (C$_{1-6}$)alkyl, (C$_{1-6}$)alkoxy, halo(C$_{1-6}$)alkyl, hydroxy, amino, nitro, carboxy, (C$_{1-6}$)alkoxycarbonyl, (C$_{1-6}$)alkoxycarbonyl(C$_{1-6}$)alkyl, (C$_{1-6}$)alkylcarbonyloxy, (C$_{1-6}$)alkylcarbonyl(C$_{1-6}$)alkylthio, arylthio, and mercapto; and,
heterocyclyl is defined as an aromatic or nonaromatic, single of fused ring group in which each ring contains up to four atoms chosen from oxygen, nitrogen, and sulfur, and each ring may be unsubstituted or substituted by up to three groups selected from halogen, (C$_{1-6}$)alkyl, (C$_{1-6}$)alkoxy, halo(C$_{1-6}$)alkyl, hydroxy, amino, nitro, carboxy, (C$_{1-6}$)alkoxycarbonyl, (C$_{1-6}$)alkoxycarbonyl(C$_{1-6}$)alkyl, aryl, (C$_{1-6}$)alkylthio, arylthio, mercapto and oxo.

3. A compound according to claim 2, wherein R is an optionally substituted (C$_{1-6}$) alkanoyl group or an optionally substituted benzoyl group.

4. A compound according to claim 1, which is selected from:
(5R)-(Z)-6-[1-(2-hydroxyethyl)-1,2,3-triazol-4-yl methylene]penem-3-carboxylic acid;
(5R)-(Z)-6-[1-(2-acetoxyethyl)-1,2,3-triazol-4-ylmethylene]penem-3-carboxylic acid;
(5R)-(Z)-6-[1-(2-trimethylacetoxyethyl)-1,2,3-triazol-4-ylmethylene]penem-3-carboxylic acid;
(5R)-(Z)-6-(1-[2-(3-carboxylpropanoyloxy)-ethyl]-1,2,3-triazol-4-ylmethylene)penem-3-carboxylic acid;
or a pharmaceutically acceptable salt or in-vivo hydrolysable ester thereof.

5. A compound according to claim 1, which is selected from:
sodium (5R)-(Z)-6-[1-(2-hydroxyethyl)-1,2,3-triazol-4-ylmethylene]penem-3-carboxylate monohydrate
sodium (5R)-(Z)-6-[1-(2-trimethylacetoxyethyl)-1,2,3-triazol-4-ylmethylene]penem-3-carboxylate,
disodium (5R)-(Z)-6-(1-[2-(3-carboxylatopropanoyloxy)ethyl]-1,2,3-triazol-4-ylmethylene)-penem-3-carboxylate, and
sodium (5R)-(Z)-6-[1-(2-hydroxyethyl)-1,2,3-triazol-4-ylmethylene)penem-3-carboxylate.

6. A compound according to claim 1, wherein the pharmaceutically acceptable salt is selected from one of the following: aluminium salts, alkali metal salts, alkaline earth metal salts, ammonium salts, substituted ammonium salts, hydroxy-lower alkylamines, di(2-hydroxyethyl)amine, tri(2-hydroxyethylamine), cycloalkylamines, dibenzylamine, N,N-dibenzylethylenediamine, 1-ephenamine, N-ethylpiperidine, N-benzyl-$\beta$- phenethylamine, dehydroabietylamine, N,N'-bishydroabietylethylene-diamine and bases of the pyridine type.

7. A compound according to claim 1, wherein the in-vivo hydrolysable ester is selected from one of the following groups: acetoxymethyl, pivaloyloxymethyl, $\alpha$-acetoxyethyl, $\alpha$-acetoxybenzyl, $\alpha$-pivaloyloxyethyl, ethoxycarbonyloxymethyl, $\alpha$-ethoxycarbonyloxyethyl, dimethylaminomethyl, diethylaminomethyl, phthalidyl and dimethoxyphthalidyl.

8. A pharmaceutically acceptable composition comprising a compound according to claim 1, in admixture or conjunction with a pharmaceutically acceptable carrier.

9. A pharmaceutically acceptable composition according to claim 8, which additionally comprises a penicillin, cephalosporin or other $\beta$-lactam antibiotic.

10. A method of treating bacterial infection, which comprises administering to a human or animal in need thereof an antibacterially effective amount or a $\beta$-lactamase inhibitory amount of a compound of general formula (II) as defined in claim 1.

11. A method according to claim 1, wherein said compound, salt or ester is administered to said human or animal in conjunction with the prior, simultaneous or subsequent administration of a penicillin, cephalosporin or other $\beta$-lactam antibiotic.

* * * * *